United States Patent [19]

Nestor, Jr. et al.

[11] Patent Number: 4,859,765
[45] Date of Patent: Aug. 22, 1989

[54] SYNTHETIC PEPTIDE SEQUENCES USEFUL IN BIOLOGICAL AND PHARMACEUTICAL APPLICATIONS AND METHODS OF MANUFACTURE

[75] Inventors: John J. Nestor, Jr., San Jose; John G. Moffatt, Los Altos; Hardy W. Chan, Belmont, all of Calif.

[73] Assignee: Syntex (U.S.A.) Inc., Palo Alto, Calif.

[21] Appl. No.: 628,678

[22] Filed: Jul. 6, 1984

Related U.S. Application Data

[62] Division of Ser. No. 542,633, Oct. 17, 1983, Pat. No. 4,493,795.

[51] Int. Cl.$^4$ ............................................. C07K 1/00
[52] U.S. Cl. ................................. 530/333; 530/326; 530/327; 530/328
[58] Field of Search ................ 260/112.5 R, 112.5 E; 530/326, 327, 328, 329, 333

[56] References Cited

U.S. PATENT DOCUMENTS

| | | | |
|---|---|---|---|
| 4,107,298 | 8/1978 | Luning | 260/112.5 R |
| 4,327,075 | 4/1982 | Luning | 260/112.5 R |
| 4,384,995 | 5/1983 | Stevens | 260/112.5 R |
| 4,493,795 | 1/1985 | Nestor, Jr. et al. | 260/112.5 E |

OTHER PUBLICATIONS

P. Y. Chou and G. E. Fasman, *Adv in Enzymology*, vol. 47, pp. 45–147 (1978).
P. Y. Chou and G. E. Fasman, *Biochemistry*, vol. 13, No. 2, pp. 212–245 (1974).

*Primary Examiner*—Delbert R. Phillips
*Attorney, Agent, or Firm*—Liza K. Toth; Tom M. Moran; Alan M. Krubiner

[57] ABSTRACT

The present invention relates to novel synthetic antigens, conjugates and antibodies based upon specific peptide sequences and the production thereof. More particularly, the invention relates to a polypeptide which is a determinant site of a protein, the polypeptide having from 8 to 20 amino acid residues, having an amino-terminal amino acid and a carboxyl-terminal amino acid, wherein the polypeptide includes:

(a) a four amino acid sequence which corresponds to the four amino acid sequence of a β-turn of the protein;
(b) a sequence of two to eight amino acid residues attached to the amino terminal (H$_2$N—) of the four amino acid sequence; and
(c) a sequence of two to eight amino acid residues attached to the carboxyl terminal (—COOH) of the four amino acid sequence, wherein the amino acid residues of subparts (b) and (c) correspond to those attached to the amino terminal and the carboxyl terminal, respectively of the β-turn of the protein, and the pharmaceutically acceptable salts of the polypeptide. The invention relates to a conjugate which comprises the polypeptide described above with a macromolecular carrier. The invention also relates to antibodies and the production thereof which are specific for the polypeptide or the conjugate of the peptide described above.

The synthetic polypeptide sequences, peptide conjugates and antibodies thereof are useful as antigens in the production of vaccines, antiviral agents, diagnostic reagents and the like, for the detection and treatment of infectious and immune diseases such as polio and cancer, and the like in mammals, particularly human beings.

5 Claims, No Drawings

SYNTHETIC PEPTIDE SEQUENCES USEFUL IN BIOLOGICAL AND PHARMACEUTICAL APPLICATIONS AND METHODS OF MANUFACTURE

This application is a divisional of pending U.S. application Ser. No. 542,633 filed Oct. 17, 1983 now U.S. Pat. No. 4,493,795.

BACKGROUND OF THE INVENTION

1. Field of the Invention

The present invention relates to the production of novel synthetic peptide (polypeptide) sequences based upon information derived from natural peptide sequences and the use of these peptide sequences as antigens in the production of vaccines, antiviral agents, diagnostic reagents and the like; for the treatment of infectious and immune diseases, such as cancer, hoof and mouth disease and the like in mammals, specifically cattle and human beings. The process includes the prediction of the antigenic determinant site ($\beta$-turn) in a protein; chemically synthesizing the peptide sequences; optionally binding the peptide to a high molecular weight carrier, such as a protein (BSA, thyroglobulin, KLH bovine gamma globulin and the like); introducing the peptide into a host as the peptide or optionally its conjugate; and immunologically producing antibodies to the peptide.

2. State of the Art

The development of synthetic peptides useful in biological applications, such as synthetic vaccines, has been under investigation for many years. The selection of and chemical or biological production of specific peptide sequences has received particular attention.

Protein structure can be visualized as a hydrophobic core of amino acids surrounded by a shell of more polar amino acids which are accessible to the solvent at the surface of the molecule. In protein molecules which interact with a receptor, such as protein hormones, the interaction between the protein and the receptor must take place at the surface-accessible sites while the hydrophobic core provides the three dimensional stability of the molecule. By arranging the critical binding site residues in the appropriate conformation, it is possible to synthesize small fragments of the protein molecule which mimic the essential surface features of the present protein and retain the appropriate biological activity. The same criteria for choosing possible binding regions of protein molecules, the most important being surface exposure and appropriate conformation can also be used to predict antigen binding sites.

Chou and Fasman, for example, reported in *Biochemistry*, vol. 13, pp 211–245 in 1974 that protein structures determined by x-ray crystallography were analyzed, and they then calculated the probabilities that each of the normal amino acid residues would be in an $\beta$-helix, $\beta$-pleated sheet or a $\beta$-turn type of structure. From these probability coefficients, they developed a method for predicting protein structure. For instance, the Chou-Fasman method for predicting the secondary structure (including $\alpha$-helix and $\beta$-pleated sheet residues) for fibroblast (F) and leukocyte (Le) interferons from the amino acid sequences is described by T. Hayes in *Biochem. and Biophys. Res. Comm.*, Vol. 95, No. 2, pp 872–9, published in 1980.

Several other methods have been applied to the prediction of the secondary structure of proteins. For example, the methods of Burgess/Sheraga (*Israel J. Chem.*, Vol. 12, pp 239–286, published in 1974, and V. I. Lim (*J. Mol. Biol.*, vol. 88, pp 857–894, published in 1974) have been used in a similar manner.

A computer program (SOAP) that progressively evaluates the hydrophilicity and hydrophobicity of a protein along its amino acid sequence is described by J. Kyte and R. F. Doolittle, *J. Mol. Biol.*, Vol. 157, pp 105–132 (1982), which is incorporated herein by reference.

T. Hopp has reported that the most hydrophilic portion of a protein molecule will be the most exposed on the surface of a protein and will constitute an antigenic determinant. Only the most hydrophilic region was reported to be an antigenic determinant (*Immuno.*, Vol. 76, No. 6, pp 3824–28, published June 1981). Hence, this predictive technique is said to yield only one antigenic determinant on the molecule. In a more recent publication, Hopp retracted this claim, see *Genetic Engineering News*, vol. 1, p 1 (1981).

Another group has reported that the same approach, i.e. calculation of regions of minimum hydrophobicity (therefore, maximum hydrophilicity) using essentially the program of Kyte and Doolittle, predicts antigenic determinants. (See, for example, R. A. Lerner, et al., *Cell*, Vol. 23, pp 309–310, published in 1981). In practice the latter group synthesized overlapping fragments constituting the entire length of the protein chain.

The preparation of antigenic hapten-carrier conjugates has been discussed by B. F. Erlanger in *Methods in Enzymology*, Vol. 70, pp. 85–104, published in 1980 by Academic Press, Inc. of New York, N.Y.; and the structure and specificity of synthetic polypeptide antigens is discussed by M. Sela in the *Ann. N.Y. Acad. Sci.*, Vol. 169, pp 23–35 (1970).

The problems associated with the development of synthetic polypeptide vaccines is discussed by A. J. Zuckerman in *Nature*, Vol. 295, pp 98–9, published Jan. 14, 1982; and by N. Wade in *Science*, Vol. 213, pp 623–8, published Aug. 7, 1981.

G. R. Dreesman et al., in *Nature*, vol. 295, pp 158–160, published on Jan. 14, 1982, discusses the selection and preparation of synthetic polypeptides which elicit an antibody response for hepatitis B surface antigen in mice after a single injection. The amino acid sequences described are different from the sequences of a natural protein.

Antibodies specific for the amino and carboxyl-terminal portions of simian virus 40 large T antigen are obtained by the immunization of rabbits with synthetic peptides corresponding to these regions. The procedures used in the preparation of antibodies specific for the ends of large T antigen with synthetic peptides as antigens are discussed by G. Walter et al., *Proc. Natl. Acad. Sci. USA*, Vol. 77, No. 9, pp 5197–5200, published in September, 1980.

The synthesis of antigenically active polypeptides and a process for their manufacture are described in U.S. Pat. Nos. 4,327,075 and 4,193,915, which are incorporated herein by reference. Additional related information is also found in the foreign patent literature; e.g., EPO Pat. Nos. 13 828 and EPO 44 710, which are incorporated herein by reference.

This invention will provide a cheaper, more efficient method of producing biologically active polypeptides or their conjugates which are useful in the diagnosis and treatment of diseases in mammals. Further, the synthetic vaccines containing polypeptides described herein would be purer and safer than conventional vaccines, which presently consist of the killed or attenuated whole virus and sometimes debris from the culture medium as well. Such synthetic vaccines will also be safer to manufacture since the risk of contamination of the site with pathogens will not be present.

SUMMARY OF INVENTION

In one aspect this invention is concerned with a polypeptide, which is a determinant site of a protein, the polypeptide having from 8 to 20 amino acid residues, having an amino-terminal amino acid and a carboxyl-terminal amino acid, wherein the polypeptide includes:
(a) a four amino acid sequence which corresponds to the four amino acid sequence of a $\beta$-turn of the protein;
(b) a sequence of two to eight amino acid residues attached to the amino terminal ($H_2N$—) of the four amino acid sequence; and
(c) a sequence of two to eight amino acid residues attached to the carboxyl terminal (—COOH) of the four amino acid sequence,
wherein the amino acid residues of subparts (b) and (c) correspond to those attached to the amino terminal and the carboxyl terminal, respectively of the $\beta$-turn of the protein, and the pharmaceutically acceptable salts of the polypeptide.

In another aspect this invention concerns synthetic polypeptides having from 8 to 20 amino acid residues and the pharmaceutically acceptable salts thereof wherein:
(a) the amino acid sequence of a naturally occurring protein or polypeptide is predicted by a prediction technique to select the four amino acid sequence comprising a $\beta$-turn;
(b) a polypeptide containing the four amino acid sequence in a $\beta$-turn with two to eight amino acid residues added to the amino terminal and two to eight amino acid residues added to the carboxyl terminal of the four amino acid sequence containing the $\beta$-turn is synthesized;
(c) the polypeptide is optionally conjugated with a macromolecular carrier; and
(d) the polypeptide or its conjugate substantially duplicates the sequence of a naturally occurring polypeptide specific antigenic determinant containing a $\beta$-turn.

In another aspect this invention is concerned with using the Chou-Fasman predictive technique to select the $\beta$-turn as is described herein.

In another aspect, this invention concerns the synthetic production of a synthetic polypeptide sequence, and optionally its conjugate, having a minimum of 8 and a maximum of 20 amino acids.

In another aspect, this invention concerns the polypeptide and polypeptide conjugate and the synthetic production of a synthetic polypeptide sequence containing a $\beta$-turn, and optionally its conjugate, having a minimum of 8, and a maximum of 20, amino acids wherein the amino-terminal amino acid of the polypeptide, $H_2N$—, is blocked using an acyl group, R—C(=O)—, particularly acetyl, $CH_3C$(=O)—, Ac—.

In another aspect, this invention concerns the polypeptide and optionally the polypeptide conjugate and the synthetic production of a synthetic polypeptide sequence containing a $\beta$-turn, and optionally its conjugate, having a minimum of 8 and a maximum of 20 amino acids wherein the carboxyl group —C(=O)—OH, on the carboxyl terminal amino acid, of the polypeptide has been converted to an amide, i.e., —C(=O)—$NH_2$.

In another aspect, this invention concerns the polypeptide and optionally the polypeptide conjugate and the synthetic production of a synthetic polypeptide sequence containing a $\beta$-turn, and optionally its conjugate, having a minimum of 8 and a maximum of 20 amino acids wherein the amino terminal of the polypeptide is blocked using an acyl group, R—C(=O)—, particularly acetyl, $CH_3C$(=O)— (Ac—), and the carboxyl group on the carboxyl terminal of the polypeptide has been converted to an amide, i.e., —C(=O)—$NH_2$.

In another aspect this invention concerns a method for treatment of an infectious or immune disease in a mammal, particularly a human being, wherein the method comprises administering to a subject in need of such treatment a therapeutically effective amount of the polypeptide sequence or a pharmaceutically acceptable salt thereof or the vaccine produced therefrom, optionally in a pharmaceutically suitable adjuvant, carrier or diluent.

In another aspect, this invention concerns a method of detecting an infectious or immune disease in a mammal, particularly a human being, wherein the method comprises using a polypeptide, or a pharmaceutically acceptable salt thereof, or optionally a peptide conjugate, or a pharmaceutically acceptable salt thereof as an immunogen to develop antibodies in a suitable host animal. Such antibodies may also serve as therapeutic agents by "passive immunization", a technique wherein partially purified immune sera from host animals or from hybridoma cell lines may be injected into a sick animal or human and have a therapeutic effect by binding to and neutralizing toxins or pathogenic organisms or tumor cells Such antibodies may be used as diagnostic reagents in antibody based assays such as the ELISA or EMIT ® assay or radioimmunoassay (RIA) techniques. The pure synthetic polypeptides (antigens), conjugates thereof, or antibodies prepared following this technique may also serve as calibration reagents in the ELISA, EMIT ® or RIA techniques.

Definitions

As used herein:

"Acyl" refers to an alkyl containing carbonyl group, e.g. R—C(=O)—, wherein R is an alkyl group having from 1 to 8 carbon atoms, such as methyl, ethyl, n-propyl, isopropyl, hexyl, octyl and the like. The acyl group usually preferred in this invention is acetyl.

"Antibody" refers to a member of a family of glycosylated proteins called immunogloblins, which can specifically combine with an antigen. Hence, the term "antibody" is a functional term, and may also be the plural form "antibodies."

"Antigen" refers to a compound which will produce antibody formation without chemical modification.

"Antigentic determinant site" refers to the actual site of antibody recognition of the antigen. The term is also used interchangeably with "epitope".

"$\beta$-turn" (also referred to as $\beta$-bend or reverse turn) refers to a structural feature of peptides and proteins involving four consecutive amino acid residues, hallmarked by the folding back on itself of the peptide chain and the presence of an intramolecular hydrogen bond, see J. A. Smith and L. G. Pease, *CRC Critical Reviews in Biochemistry*, vol. 8, pp 317-400, (October 1980), which is incorporated herein by reference.

"Carrier" usually refers to a high molecular weight (macromolecular) polymeric material (usually a protein), which alone or when conjugated with a polypeptide (hapten) will produce antibody formation. It may also be referred to as a substrate or protein substrate upon which an enzyme acts.

"Conjugate" refers to a polypeptide (or hapten) chemically-bonded to a high molecular weight (macromolecular) carrier or (substrate), such as the prolactin antigen-bovine gammaglobulin conjugate formed by methods known in the art.

"ELISA" refers to an enzyme-linked-immunosorbent assay which employs an antibody or antigen bound to a solid phase and an enzyme-antigen or enzyme-antibody conjugate to detect and quantify the amount of antigen or antibody present in a sample. A description of the ELISA technique is found in Chapter 22 of the 4th Edition of *Basic and Clinical Immunology* by D. P. Sites et al., published by Lange Medical Publications of Los Altos, Calif. in 1982, and in U.S. Pat. Nos. 3,654,090; 3,850,752; and 4,016,043, which are all incorporated herein by reference.

"EMIT ®" refers to an enzyme-multiplied immunoassay technique which uses (1) an enzyme-labeled hapten, (2) specific antibody to the hapten, (3) pretreatment reagent, (4) buffered-enzyme substrate and (5) standards to detect the amount of an unknown in a sample. A description of the EMIT technique is found in *Enzyme Immunoassay*, edited by E. T. Maggio, published in 1980 by CRC Press, Inc., Boca Raton, Fla., particularly on pp. 141-150, 234-5 and 242-3.

"Enzyme" refers to a protein capable of accelerating or producing by catalytic action some change in a substrate for which it is often specific. Enzymes are divided into six main groups: oxidoreductases, transferases, hydrolases, lyases, isomerases and ligases.

"Enzyme labeled" refers to an enzyme which has been further labeled with a means of detection, such as a fluorescent molecule, a radioactive group or the like.

"Epitope" refers to that portion of a molecule which is specifically recognized by an antibody. It is also referred to as the determinant site or antigenic determinant site.

"Hapten" refers to a compound, usually of low molecular weight, for which antibodies can be formed by bonding of the compound to another compound or material, such as a protein, which has antigenic properties.

"Ligand" refers to any molecule which can bind to a receptor, for our purposes an antibody combining site. Such a molecule is normally antigenic or haptenic.

"Lower alkyl" refers to a straight or branched chain saturated hydrocarbon group having from 1 to 4 carbon atoms such as, for example, methyl, ethyl, n-propyl, iso-propyl, n-butyl, iso-butyl, sec-butyl and tert-butyl.

"Peptide" or "polypeptide" refers to any member of a class of compounds of relatively low molecular weight which yield two or more amino acids on hydrolysis. Formed by the loss of water from the —NH$_2$ and —COOH groups of adjacent amino acids, they are known as di-, tri-, tetra- (etc.) peptides, depending on the number of amino acids in the molecule. Peptides form the constituent parts of proteins, and may be linear or cyclic.

"Pharmaceutically acceptable salt" refers to salts that retain the desired biological activity of the parent compound and do not impart any undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, pamoic acid, alginic acid, polyglutamic acid, naphthalenesulfonic acids, naphthalenedisulfonic acids, polygalacturonic acid; (b) salts with polyvalent metal cations such as zinc, calcium, barium, magnesium, aluminum, copper, cobalt, nickel, cadmium, and the like; or with an organic cation formed from N, N'-dibenzylethylenediamine or ethylenediamine; or (c) combinations, of (a) and (b), e.g. a zinc tannate salt and the like.

"Protein" refers to any one of a group of complex organic nitrogenous compounds, widely distributed in plants and animal tissue. Proteins are essentially combinations of amino acids in peptide linkages.

"Radioimmunoassay" or "(RIA)" refers to an antibody based assay in which the ligand to be measured displaces or competes for binding with a radio-labelled ligand in an antibody-ligand complex. The complex is separated and the percentage of radio-ligand bound gives a measure of the amount of assayable cold (non-radioactive) ligand.

"Receptor" for our purposes refers to a specific region of an antibody with the capability of combining specifically with an antigen. It can also refer to a protein which can bind other ligands and thereby cause biological effects.

"Vaccine" usually refers to a suspension or solution of attenuated or killed microorganisms (bacteria, viruses, etc.) or synthetic polypeptides or conjugates administered for the prevention, amelioration or treatment of infectious diseases via stimulation of the production of specific antibodies against the disease causing organism. In this application, vaccine also includes the polypeptide sequences and optionally the polypeptide conjugates described and claimed herein for use in both active and passive immunization.

The definitions of additional terms in this area may be found in *Dorland's Illustrated Medical Dictionary*, 25th Ed., published by W. B. Saunders Company of Philadelphia, Pa. in 1974, and an overview of diagnostic applications of enzyme receptors is found in *Enzyme Immunoassay*, edited by E. T. Maggio, supra, both of which are incorporated herein by reference.

As set forth above and for convenience in describing this invention, the conventional abbreviations for the various common amino acids are used as generally accepted in the peptide art as recommended by the IUPAC-IUB Commission on Biochemical Nomenclature, *Biochemistry*, 11, 1726 (1972) and represent L-amino acids with the exception of the achiral amino acid glycine. All peptide sequences mentioned herein are written according to the generally accepted convention whereby the N-terminal (or amino-terminal) amino acid is on the left and the C-terminal (carboxyl-terminal) amino acid is on the right.

As used herein, the following abbreviations are used for the amino acids described in this application:

| | |
|---|---|
| Alanine | Ala |
| Arginine | Arg |
| Asparagine | Asn |
| Aspartic Acid | Asp |
| Cysteine | Cys |

| -continued | |
|---|---|
| Glutamine | Gln |
| Glutamic Acid | Glu |
| Glycine | Gly |
| Histidine | His |
| Isoleucine | Ile |
| Leucine | Leu |
| Lysine | Lys |
| Methionine | Met |
| Phenylalanine | Phe |
| Proline | Pro |
| Serine | Ser |
| Threonine | Thr |
| Tryptophan | Trp |
| Tyrosine | Tyr |
| Valine | Val |

DETAILED DESCRIPTION OF THE INVENTION AND PREFERRED EMBODIMENTS

Preferred embodiments of the present invention. include the polypeptides having following the amino acid sequences, H—Tyr—Gly—Ala—Ser—Asp—Ser—Asn—Val—Tyr—Asp—Leu—Cys—OH, H—Tyr—Asp—Thr—Ser—Asp—Ser—Asp—Tyr—His—Leu—Cys—OH, H—Leu—Pro—Ile—Cys—Pro—Gly—Gly—Ala—Ala—Arg—Cys—Gly—OH, or H—Gly—Cys—Arg—Ile—Ile—His—Asn—Asn—Asn—Cys—OH, and the pharmaceutically acceptable salts thereof.

Subgroups of the above embodiments include the polypeptide described wherein the amino-terminal amino acid is blocked using an acyl group.

Subgroups of the above embodiments include the polypeptide described wherein the carboxyl-terminal amino acid has been converted to an amide group.

Subgroups of the above embodiments include the polypeptide described wherein the amino-terminal amino acid is blocked using an acyl group and the carboxyl-terminal amino acid has been converted to an amide group, respectively.

An embodiment of the present invention includes a conjugate which comprises a polypeptide described herein conjugated with a macromolecular carrier.

A preferred subgroup includes the conjugate wherein the macromolecular carrier is selected from the group consisting of polysaccharides, polymeric amino acids and the copolymers thereof, enzymes and proteins, particularly an enzyme.

Preferred conjugates include those of the polypeptides specifically described hereinabove.

A preferred subgroup includes the conjugate, wherein in the polypeptide the amino-terminal amino acid is blocked using an acyl group, particularly an acetyl group.

A preferred subgroup includes the conjugate wherein in the polypeptide the carboxyl-terminal amino acid has been converted to an amide group.

A preferred subgroup includes the conjugate wherein in the polypeptide, the amino-terminal amino acid is blocked using an acyl group and the carboxyl-terminal amino acid has been converted to an amide group, respectively.

An embodiment of the present invention includes a method of producing the polypeptide described herein which comprises adding from two to eight amino acid residues to each of the carboxyl-terminal amino acid and amino-terminal amino acid, respectively, of a four amino acid sequence having a β-turn of a naturally occurring protein or polypeptide.

A subgroup includes the method wherein the four amino acid sequence of the β-turn is determined to have a β-turn by a prediction technique, particularly the Chou-Fasman technique.

An embodiment of the present invention further includes the method described above which includes the step of conjugating the polypeptide with a macromolecular carrier.

An embodiment of the present invention includes a method of producing an antibody specific for the polypeptide or conjugate described above which comprises challenging a host animal with the polypeptide or the conjugate to elicit the production of the antibody and collecting the antibody.

An embodiment of the present invention includes an antibody specific for the conjugate described hereinabove, and for a protein containing, as a determinant site, a polypeptide sequence which corresponds to the β-turn sequence of the polypeptide.

Preferred subgroups include the method of producing conjugates of the polypeptides described herein, and the pharmaceutically acceptable salts thereof.

An embodiment of the present invention includes an antibody specific for the polypeptide described herein, and for a protein containing, as a determinant site, a polypeptide sequence which corresponds to the β-turn sequence of the polypeptide.

An embodiment of the present invention includes an antibody specific for the conjugate described herein, and for a protein containing, as a determinant site, a polypeptide sequence which corresponds to the β-turn sequence of the polypeptide.

A method for treating an infectious or immune disease in a mammal which comprises administering to a subject in need of such treatment a therapeutically effective amount of the polypeptide or conjugate described herein or a pharmaceutically acceptable salt thereof, optionally in a pharmaceutically suitable adjuvant.

A method for treating an infectious or immune disease in a mammal which comprises administering to a subject in need of such treatment a therapeutically effective amount of the antibody of the polypeptide or conjugate described herein above or a pharmaceutically acceptable salt thereof, optionally in a pharmaceutically suitable adjuvant.

A method for treating an infectious or immune disease in a mammal which comprises administering to a subject in need of such treatment a therapeutically effective amount of the antibody described herein or a pharmaceutically acceptable salt thereof, optionally in a pharmaceutically suitable adjuvant.

The method of treating infectious or immune disease wherein the mammal is a human being.

An embodiment of the present invention includes a pharmaceutical composition useful for treating an immune or infectious disease which comprises a therapeutically effective amount of the polypeptide or polypeptide conjugate described herein above in admixture with a pharmaceutically acceptable adjuvant.

A pharmaceutical composition useful for treating an immune or infectious disease which comprises a therapeutically effective amount of the antibody of the polypeptide or conjugate described herein in admixture with a pharmaceutically acceptable adjuvant.

Subgroups include the specific polypeptides or polypeptides conjugates described herein.

A method for determining the presence in a sample of a protein having, as a determinant site, a polypeptide sequence which corresponds to the β-turn sequence of the polypeptide described herein, which method comprises:
(a) combining the sample in an aqueous medium with the antibody of the polypeptide or conjugate described herein and the conjugate of an enzyme as described herein;
(b) determining the enzyme activity of the combination, which activity is related to the presence of the protein in the sample.

A subgroup includes the method which further includes the comparing the enzyme activity of step (b) immediately above with the enzyme activity of an assay medium having a known amount of the protein.

A composition useful in the comparison of the enzyme activity of step (b) above, as the assay medium having a known amount of the protein, which composition comprises an assay medium having a known amount of the polypeptide described herein.

An immunoassay method for determining the presence of a protein containing, as a determinant site, a polypeptide sequence which corresponds to the β-turn sequence of the polypeptide described herein, which method includes employing as a reagent an antibody specific for the protein or a labeled antibody specific for the protein, the improvement which comprises employing the antibody of the polypeptide described herein as the antibody specific for the protein or as the labeled antibody specific for the protein.

A kit for an assay for the determination of a protein having, as a determinant site, the polypeptide sequence which corresponds to the β-turn sequence of the polypeptide described herein in a sample containing such protein, which kit includes as a reagent in such assay, in a packaged combination in predetermined ratio, an antibody specific for the protein, or a labeled antibody specific for the protein, the improvement which comprises employing the antibody of the polypeptide described herein as the antibody specific for the protein.

PROCESS FOR PREPARATION

Selection of the Antigentic Determinant Site

A number of methods dealing with methods for empirical prediction of protein structure and their applications have been published, see, for example, B.W. Matthews, *Biochim. Biophys. Acta*, vol. 405, p 442 (1975) which is incorporated herein by reference.

The Chou and Fasman (supra) correlative method is a widely used procedure for predicting the conformation of the peptide backbone in proteins. As part of this technique, Chou and Fasman established a set of numerical values to predict those amino acid sequences which would have a probability of being in a β-turn. See Table 1 and P. Y. Chou and G. E. Fasman, *Adv in Enzymology*, vol. 47, pp 45-147 (1978), which is incorporated herein by reference.

TABLE I

Frequency Hierarchies of Amino Acids in the β-Turns of 29 Proteins[a]

| i | | i + 1 | | i + 2 | | i + 3 | | $P_t$ | | $Pt_2$ | |
|---|---|---|---|---|---|---|---|---|---|---|---|
| Asn | 0.161 | Pro | 0.301 | Asn | 0.191 | Trp | 0.167 | Asn | 1.56 | Pro | 2.04 |
| Cys | 0.149 | Ser | 0.139 | Gly | 0.190 | Gly | 0.152 | Gly | 1.56 | Gly | 1.63 |
| Asp | 0.147 | Lys | 0.115 | Asp | 0.179 | Cys | 0.128 | Pro | 1.52 | Asp | 1.61 |
| His | 0.140 | Asp | 0.110 | Ser | 0.125 | Tyr | 0.125 | Asp | 1.46 | Asn | 1.56 |
| Ser | 0.120 | Thr | 0.108 | Cys | 0.117 | Ser | 0.106 | Ser | 1.43 | Ser | 1.52 |
| Pro | 0.102 | Arg | 0.106 | Tyr | 0.114 | Gln | 0.098 | Cys | 1.19 | Lys | 1.13 |
| Gly | 0.102 | Gln | 0.098 | Arg | 0.099 | Lys | 0.095 | Tyr | 1.14 | Tyr | 1.08 |
| Thr | 0.086 | Gly | 0.085 | His | 0.093 | Asn | 0.091 | Lys | 1.01 | Arg | 1.05 |
| Tyr | 0.082 | Asn | 0.083 | Glu | 0.077 | Arg | 0.085 | Gln | 0.98 | Thr | 0.98 |
| Trp | 0.077 | Met | 0.082 | Lys | 0.072 | Asp | 0.081 | Thr | 0.96 | Cys | 0.92 |
| Gln | 0.074 | Ala | 0.076 | Thr | 0.065 | Thr | 0.079 | Trp | 0.96 | Gln | 0.84 |
| Arg | 0.070 | Tyr | 0.065 | Phe | 0.065 | Leu | 0.070 | Arg | 0.95 | Glu | 0.80 |
| Met | 0.068 | Glu | 0.069 | Trp | 0.064 | Pro | 0.068 | His | 0.95 | His | 0.77 |
| Val | 0.062 | Cys | 0.053 | Gln | 0.037 | Phe | 0.065 | Glu | 0.74 | Ala | 0.64 |
| Leu | 0.061 | Val | 0.048 | Leu | 0.036 | Glu | 0.064 | Ala | 0.66 | Phe | 0.62 |
| Ala | 0.060 | His | 0.047 | Ala | 0.035 | Ala | 0.058 | Met | 0.060 | Met | 0.51 |
| Phe | 0.059 | Phe | 0.041 | Pro | 0.034 | Ile | 0.056 | Phe | 0.60 | Trp | 0.48 |
| Glu | 0.056 | Ile | 0.034 | Val | 0.028 | Met | 0.055 | Leu | 0.59 | Val | 0.43 |
| Lys | 0.055 | Leu | 0.025 | Met | 0.014 | His | 0.054 | Val | 0.50 | Leu | 0.36 |
| Ile | 0.043 | Trp | 0.013 | Ile | 0.013 | Val | 0.053 | Ile | 0.47 | Ile | 0.29 |

[a]i, i + 1, i + 2, and i + 3 represent the frequencies of the first, second, third and fourth residues, respectively, in a reverse β-turn based on all four positions of a reverse turn. $Pt_2$ is the conformational potential of a residue in a β-turn based on the second and third positions of a reverse turn. This frequency table was based on 408 β-turns in 29 proteins.

The technique then multiplies the probabilities shown in the above table of each amino acid in a particular quartet of amino acids to be at position "i" in a β-turn times the probability of the amino acid at position i+1 to be in position "i+1", etc.

Thus, for the sequence of amino acids 82 to 85 of FMDV-UP$_{th}$, that is, His-Glu-Gly-Asp, the following calculation is made:

$$P_{turn} = f(\text{amino acid at position } i) \times$$
$$f(\text{amino acid at position } i + 1) \times$$
$$f(\text{amino acid at position } 1 + 2) \times$$
$$f(\text{amino acid at position } i + 3).$$

Then substituting the amino acids numbered 82 to 85, $$P_{turn} = f(\text{His}) \times f(\text{Glu}) \times f(\text{Gly}) \times f(\text{Asp}).$$

Next inserting the probabilities of these amino acids, $$P_{turn} = f(0.14) \times f(0.07) \times f(0.19) \times f(0.081); \text{ thus}$$

$$P_{turn} = 1.5 \times 10^{-4}$$

Chou and Fasman indicate that for prediction of a $\beta$-turn by this method the calculated probability of a $\beta$-turn should be greater than or equal to $0.75 \times 10^{-4}$. Therefore, a $\beta$-turn would be predicted for the amino acid sequence: His-Glu-Gly-Asp.

All possible quartets of adjacent amino acid residues in the protein are examined in this manner, and those regions meeting the $P_{turn}$ greater than or equal to $0.75 \times 10^{-4}$ criterion are chosen as potential $\beta$-turns and therefore biologically active epitopes. Regions on both sides of the predicted $\beta$-turn (usually 2 to 8 amino acids, preferably 5) are then synthetically added to provide additional stabilization to the $\beta$-turn via h In this particularly preferred method the α-amino function of the amino acids is protected by an acid or base sensitive group. Such protecting groups should have the properties of being stable to the conditions of peptide linkage formation, while being readily removable without destruction of the growing peptide chain or racemization of any of the chiral centers contained therein. Suitable protecting groups are t-butyloxycarbonyl (Boc), benzyloxycarbonyl (Z), biphenylisopropyloxycarbonyl, t-amyloxycarbonyl, isobornyloxycarbonyl, alpha, alpha-dimethyl-3,5-dimethoxybenzyloxycarbonyl, o-nitrophenylsulfenyl, 2-cyano-1,1-dimethyl-ethoxycarbonyl, 9-fluorenylmethoxycarbonyl and the like, especially t-butyloxycarbonyl (Boc).

Particularly preferred side chain protecting groups are, for arginine: nitro, p-toluenesulfonyl-, 4-methoxybenzenesulfonyl, Z, Boc and adamantyloxycarbonyl; for tyrosine benzyl, o-bromobenzyloxycarbonyl, 2,6-dichlorobenzyl, isopropyl, cyclohexyl, cyclopentyl and acetyl; for serine: benzyl and tetrahydropyranyl; for histidine: benzyl, p-toluenesulfonyl and 2,4-dinitrophenyl.

The carboxyl-terminal amino acid (C-terminal) [—C(=O)—OH] is attached to a suitable solid support. Suitable solid supports useful for the above synthesis are those materials which are inert to the reagents and reaction conditions of the stepwise condensation-deprotection reactions, as well as being insoluble in the media used. Suitable solid supports are chloromethylpolystyrene-divinylbenzene polymer, hydroxy-methyl-polystyrene-divinylbenzene polymer, and the like, especially chloromethyl-polystyrene-1% divinylbenzene polymer. For the special case where the carboxyl-terminal amino acid of the peptide becomes an amide [—C(=O)—NH$_2$], a particularly useful support is the benzhydrylamino-polystyrene-divinylbenzene polymer described by P. Rivaille, et al., *Helv. Chim. Acta.*, 54, 2772 (1971). The attachment to the chloro- methyl polystyrene-divinylbenzene type of resin is made by means of the reaction of the N$^\alpha$-protected amino acid, especially the Boc-amino acid, as its cesium, tetramethylammonium, triethylammonium, 4,5-diazabicyclo[5.4.0]undec-5-ene, or similar salt in ethanol, acetonitrile, N,N-dimethylformamide (DMF), and the like, especially the cesium salt in DMF, with the chloromethyl resin at an elevated temperature, for example between about 40° and 60° C., preferably about 50° C., for from about 12 to 48 hours, preferably about 24 hours. The N$^\alpha$-Boc-amino acid is attached to the benzhydrylamine resin by means of an N,N'-dicyclohexylcarbodiimide (DCC)/1-hydroxybenzotriazole (HBT) mediated coupling for from about 2 to about 24 hours, preferably about 12 hours at a temperature of between about 10° and 50° C., preferably 25° C. in a solvent such as dichloromethane or DMF, preferably dichloromethane. The coupling of successive protected amino acids can be carried out in an automatic polypeptide synthesizer as is well known in the art. The removal of the N$^\alpha$-protecting groups may be performed in the presence of, for example, a solution of trifluoroacetic acid in methylene chloride, hydrogen chloride in dioxane, hydrogen chloride in acetic acid, or other strong acid solution, preferably 50% trifluoroacetic acid in dichloromethane at about ambient temperature. Base labile protecting groups maybe removed by treatment with a base such as piperidine in DMF or dioxane. Each protected amino acid is preferably introduced in approximately 2.5 molar excess and the coupling may be carried out in dichloromethane, dichloromethane/DMF mixtures, DMF and the like, especially in methylene chloride at about ambient temperature. The coupling agent is normally DCC in dichloromethane but may be N,N'-di-iso-propylcarbodiimide or other carbodiimide either alone or in the presence of HBT, N-hydroxysuccinimide, other N-hydroxyimides or oximes. Alternately, protected amino acid active esters (e.g. p-nitrophenyl, pentafluorophenyl and the like) or symmetrical anhydrides may be used.

At the end of the solid phase synthesis, the polypeptide is either carried through another deprotection and neutralization cycle followed by acylation, preferably acetylation with acetic anhydride to yield an N-acetyl (N-Ac) blocked amino-terminal or it may be removed from the resin directly. If the carboxyl [—C(=O)—OH] terminal is to be blocked as the amide, the peptide may be either be synthesized on the benzhydrylamino-polystyrene resin, which gives the amide directly or it may be removed from the resin by ammonolysis with, for example, ammonia/methanol or ammonia/ethanol, at a temperature of from about 0° to about 50° C., preferably about 25° C. for about 12 to about 48 hr, preferably about 18 hr. If a peptide with a free amino-terminal and a carboxyl-terminal is desired, the peptide may be directly removed from the resin by treatment with anhydrous liquid hydrogen fluoride in the presence of a radical scavenger such as anisole. The amino- or carboxyl-blocked (protected) peptides, either on the resin or removed from the resin by ammonolysis, are similarly deprotected by treatment with anhydrous liquid hydrogen fluoride. In cases where base labile protection of the N$^\alpha$ function is used in conjunction with t-butyl based side chain protection, the final resin removal and deprotection step may be performed with trifluoroacetic acid.

Other means of removal of the (side chain) protecting groups from the polypeptide are treatment with hydrogen fluoride/pyridine complex, treatment with tris(trifluoroacetyl)boron and trifluoroacetic acid, by reduction with hydrogen and palladium on carbon or polyvinylpyrrolidone, or by reduction with sodium in liquid ammonia, preferably with liquid hydrogen fluoride, and anisole at a temperature between about −10° and +10° C., preferably about 0° C., for between about 15 minutes and 1 hour, preferably about 30 minutes. The latter treatment (HF/anisole) may be used for simultaneous cleavage from the resin and deprotection to yield free —CO$_2$H when a normal benzylester linkage has been used or to form a CO—NH$_2$ when a benzhydrylamino linkage has been used. For the amide terminal peptides on the benzhydrylamine resins, the resin cleavage and deprotection steps may be combined in a single step utilizing liquid hydrogen fluoride and anisole as described above. The fully deprotected polypeptide is then purified by a sequence of chromatographic steps employing any or all of the following types: ion exchange on a weakly basic resin in the acetate form; hydrophobic adsorption chromatography on underivatized polystyrene-divinylbenzene (for example Amberlite XAD); silica gel adsorption chromatography; ion exchange chromatography on carboxymethylcellulose; partition chromatography, e.g. on Sephadex G-25, or countercurrent distribution; high performance liquid chromatography (HPLC), especially reverse phase HPLC on octyl- or octadecylsilyl-silica bonded phase column packing.

Thus in an additional aspect, the invention is concerned with free and protected (or blocked) synthetic polypeptides having 8 to 20 amino acid residues, i. e.; for the human growth hormone fragment:

H-[Ala-Ser-Asp-Ser-Asn-Val-Tyr-Asp]-OH (unprotected or free polypeptide);

Ac-[Ala-Ser-Asp-Ser-Asn-Val-Tyr-Asp]-OH [amino-terminal (—NH$_2$) protected as Ac—NH—)];

H-[Ala-Ser-Asp-Ser-Asn-Val-Tyr-Asp-]NH$_2$; [carboxyl-terminal [—C(=O)—OH] protected as the amide, —C—(=O)—NH$_2$]; and Ac-[Ala-Ser-Asp-Ser-Asn-Val-Tyr-Asp]-NH$_2$; [amino-terminal protected as Ac—NH—, and carboxyl-terminal protected as —C(=O)—NH$_2$].

(For conjugation with a high molecular weight carrier of the polypeptide where both the amino-terminal and the carboxyl-terminal have been protected, a chemically reactive group should be present within the polypeptide chain, e.g., —OH of tyrosine, for the chemical attachment of the conjugate.)

Thus, in another aspect the present invention relates to a method for preparing these compounds of the which process comprises:

(i) coupling fragments; or (ii) removing protecting groups and, optionally, covalently bound solid support from a protected polypeptide to afford a compound of the aforementioned polypeptide sequences or a salt thereof, and optionally (iii) converting a compound of the aforementioned polypeptide sequences to a pharmaceutically acceptable salt thereof, or (iv) converting a salt of a compound of the aforementioned polypeptide sequences to a pharmaceutically acceptable different salt thereof, or (iv) decomposing a salt of a compound of the aforementioned polypeptide sequences to a free polypeptide of the aforementioned polypeptide sequences.

CONJUGATION OF POLYPEPTIDES TO PROTEIN CARRIERS

A. Functional Groups—The polypeptides described herein may be coupled to protein or high molecular weight (macromolecular) polymeric carriers (or substrates) through several types of functional groups on the antigen, e.g. (a) $\alpha$ or $\epsilon$-amino groups, (b) $\alpha$, $\beta$, or $\gamma$-carboxyl groups, (c) thiol (—SH) groups, (d) aromatic rings (e.g., Tyr, His)

B. Specific Techniques—

1. $\alpha$- or $\epsilon$-amino groups

Several coupling methods are available.

a. The carboxyl functional groups on a carrier may be activated with carbodiimides (especially water soluble carbodiimides (WSC) such as N-ethyl-N'-(3-dimethylaminopropylcarbodiimide), isoxazolium salts (e.g., Woodwards Reagent K), 1-ethoxycarbonyl-2-ethoxy-1,2-dihydroquinoline (EEDQ), active ester forming reagents (to yield N-hydroxysuccinimide esters, 1-hydroxybenzotriazole esters, nitrophenyl esters, pentafluorophenyl esters, etc.), reagents yielding acid chlorides (e.g., PCl$_5$, but only for non-protein carriers), reagents yielding mixed anhydrides (e.g., isobutylchloroformate, acetic anhydride, pivalic anhydride).

The free amino function of the synthetic antigen (either $\alpha$-amino function or $\epsilon$-amino function of lysine) is then allowed to react with the activated carboxyl function of the carrier in an aqueous buffer (pH may be from about 6.5 to 9, optimally about 8) or in a mixed organic/aqueous buffer system (e.g., DMF/water, pH 8). For non-protein carriers, an organic solvent (e.g., DMF) may be used. Especially useful techniques in this class are concurrent activation of the protein carrier with WSC and coupling with antigen in aqueous buffer or preparation of the p-NO$_2$-phenyl ester of a succinylated protein carrier followed by coupling with the antigen in aqueous buffer.

b. The amino function(s) on the synthetic antigen may be crosslinked with amino functions on the carrier molecule by reaction with gluteraldehyde in aqueous solution on mixed organic/aqueous solution (pH~7) at room temperature.

c. The amino function(s) on the synthetic antigen may be crosslinked with amino functions on the carrier molecule by reaction with bifunctional crosslinking reagents such as dimethylsuberimidate, phenyldiisocyanate, phenyldiisothiocyanate, difluorodinitrobenzene, or cyanic chloride.

2. $\alpha$, $\beta$, or $\gamma$ Carboxyl Groups

The carboxyl functions on the synthetic antigen will be activated by the techniques listed under Section B.(1) a for carboxyl activation. The activated carboxyl functions will then be reacted with the amino functions on a suitable carrier molecule using the aqueous or mixed organic/aqueous buffer conditions described above.

3. Thiol (—SH) Groups

The —SH groups on the synthetic antigen (incorporated as cysteinyl or homocysteinyl residues on or in the polypeptide chain) will be reacted with suitable carriers which have been modified by the incorporation of maleimide functions. The —SH function inserts specifically into the double bond of the maleimide function and yields an antigen-carrier complex in which the carrier has retained a monomeric nature. The SH function may be incorporated into the antigen by either incorporation of a Cys (or homo-Cys) residue in $\alpha$-amino acid linkage, or by reaction of an amino function ($\alpha$-amino or $\epsilon$-amino of lysine) with cysteine thiolactone. Alternatively, the —SH function on the antigen may be activated as the 2- or 4-thiopyridyldisulfide and bonded to the —SH groups on a suitable carrier. This sequence may also be reversed with the carrier —SH activated as the thiopyridyldisulfide.

4. Aromatic rings

The aromatic rings of Tyr and His may be crosslinked to the aromatic rings of Tyr and His residues of proteins by means of bis-diazotized aromatic compounds (e.g., bis-diazotized-benzidine or bis-diazotized o-anisidide). This reaction is performed on an aqueous or mixed organic/aqueous solution of the antigen and carrier.

C. Suitable Protein Substrates (Carriers)

Suitable substrates (carriers) for this process, include but are not limited to the following, large, slowly metabolized macromolecules such as proteins; polysaccharides, such as latex functionalized sepharose, agarose, cellulose, cellulose beads and the like; polymeric amino acids, such as polyglutamic acid, polylysine and the like; and amino acid co-polymers. Especially useful protein substrates are serum albumins, tetanus toxoid, keyhole limpet hemocyanin, immunoglobulin molecules, thyroglobulin, ovalbumin, and other proteins well known to those skilled in the art. Such proteins may be used in their native form or their function group content may be modified by succinylation of Lys residues or reaction with Cys-thiolactone. A sulfhydryl group may also be incorporated into the carrier (or antigen) by reaction of amino functions with 2-iminothiolane or the N-hydroxysuccinimide ester of 3-(4-dithiopyridyl) propionate. Suitable carriers may also have been modified to incorporate spacer arms (such as hexamethylene diamine or other bifunctional molecules of similar size) for attachment of the antigen.

For a recent review of these techniques see B. F. Erlanger in *Methods of Enzymology*, vol. 70, p 85ff (1980), "The Preparation of Antigenic Haptene - Carrier Conjugates - A Survey".

Vaccine Preparation Techniques

Vaccine preparation techniques are generally known in the art as described by J. I. Duffy (ed.) in *Vaccine Preparation Techniques*, published by Noyes Data Corporation of Park Ridge, N.J. in 1980, and references cited therein, all of which are incorporated herein by reference. More specifically, in this application the therapeutic agent of the vaccine is generally considered to be the polypeptide sequence, the polypeptide conjugate or the antibody to the polypeptide or the polypeptide conjugate as described herein.

Introducing the Peptide Sequence into a Host and Producing Antibodies

The polypeptide sequence produced above is then introduced into a mammalian host. This is usually accomplished by subcutaneous injection into mammals as a solution in saline which has been emulsified with complete Freund's adjuvant. Monthly booster injection of antigen in incomplete Freund's adjuvant are made, and the animals are bled monthly (one week prior to booster) to obtain sera for characterization. Alternatively Freud's adjuvent can be replaced by synthetic adjuvants such as N-Ac-muramyl-L-Ala-D-IGln or its analogs. Antibodies may be prepared by a number of known methods, see, for instance, U.S. Pat. Nos. 4,082,735 and 4,082,736, which are incorporated herein by reference.) Suitable hosts include for example, monkeys, cattle, sheep, goats, swine, dogs, cats, rabbits, chickens, rats, guinea pigs, mice and the like.

Collecting the Antibodies

The antibodies are collected by bleeding the animal, either partially (about 10% of blood volume) or by a complete exsanguination. The whole blood is allowed to clot at 25° C. for several hrs. This aqueous ammonium sulfate solution is added to achieve 40% by weight of aqueous solution, and the IgG fraction precipitates. The clear serum is separated from the clot by centrifugation and is diluted with 0.9% saline to the desired concentration. Alternately, the antibodies may be further purified by affinity chromatography or salt precipitation prior to dilution. Thus, aqueous ammonium sulfate solution is added to achieve 40% by weight of aqueous solution, and the IgG fraction precipitates. The precipitate is collected by centrifugation and resuspended in saline or buffer solution to the desired concentration.

The purified antibody fraction may be further modified for use in diagnostic assay systems. Such modification may encompass linkage with enzymes such as lipozyme, lactoperoxidase, et al. for use in ELISA assays. The antibody may be modified with fluorescent moieties whose fluorescence may be quenched or enhanced upon binding of the antibody and the antigen. These techniques for assaying the extent of the antibody-antigen interaction are known in the art. The essential first step is, however, the preparation of a suitably immunogenic polypeptide (vaccine) for administration to the animals so that a population of high affinity antibodies will be obtained.

ANTISERUM CHARACTERIZATION

The antisera obtained are characterized by means of an ELISA assay. (see, Maggio, supra, for more detail, and U.S. Pat. Nos. 3,654,090; 3,850,752; and 4,016,043, which are incorporated herein by reference). Briefly, the polypeptide (antigen) or a conjugate of the polypeptide (antigen) to a non-cross reacting carrier protein, e.g., bovine serum albumin is prepared as described above and a solution of this conjugate is dried down in individual wells of a polystyrene microwell plate. Into these wells are placed doubling dilutions of the serum sample containing antibodies against the antigen. After an incubation period of about 8 hr, the well contents are decanted, the wells are washed and a commercially available enzyme-linked goat-anti-rabbit-IgG antibody reagent (to assay antibodies raised in rabbits) is introduced. In the case described here the enzyme used is horseradish peroxidase. After an 8 hr incubation period, the well contents are decanted and the wells are washed. A solution containing the chromogen, 2,2'-azino-di(3-ethyl-benzthiazolinesulfonic acid) ammonium salts (ABTS) and $H_2O_2$, is added to the wells and the color is developed and quantitated by absorption at 415 nm in a UV spectrophotometer. Increasing optical density (OD) readings indicate greater antibody response. An OD of greater than 1 indicates a moderate to strong response.

For example, in the case cited herein the response mounted against the prolactin fragment, H-Gly-Cys-Arg-Ile-Ile-His-Asn-Asn-Asn-Cys-OH was moderate with OD values measured at 3 months post-injection of 1.4 in one animal and 0.4 in another.

Chemically Synthesizing the Polypeptide in Therapeutic Quantities

After being chosen by the method described (supra) the polypeptides are synthesized by solid phase or solution phase techniques well-known to those skilled in the art. References to texts describing these techniques and general descriptions of these techniques have been provided (supra). Using these techniques, the desired polypeptides may be prepared on gram, kilogram, or larger scale. More detailed descriptions are found in the examples.

E. UTILITY AND ADMINISTRATION

In the practice of the method of this invention an effective amount of a compound of the invention or a pharmaceutical composition containing same is administered to the subject in need of, or desiring, such treatment. These compounds or compositions may be administered by any of a variety of routes depending upon the specific end use, including particularly parenterally (including subcutaneous, intramuscular and intravenous administration). The most suitable route in any given case will depend upon the use, particular active ingredient, the subject involved, and the judgment of the medical practitioner. The compound or composition may also be administered by means of slow-release, depot or implant formulations as is well known in the art. The polypeptides, polypeptide conjugates and antibodies described herein are usually administered in amounts of 1 to 100 μg per kg of body weight, particularly in amounts of 40–60 μg.

For active immunity, the polypeptide or the polypeptide conjugate is administered to produce the antibodies in the subject in need of treatment. In passive immunity, partially purified sera containing antibodies from host animals is introduced into the subject to produce a therapeutic effect by binding to and neutralizing the toxins, pathogenic organisms or tumor cells.

The polypeptides, polypeptide conjugates and antibodies produced to the polypepties and polypeptide conjugates have a variety of uses in animal and human health disease diagnosis and treatment. These include, for example, treatment of any disease of the immune system for which antibodies are produced and certain cancers, such as leukemia. Infectious diseases such as hepatitis, polio, diphtheria, tetanus, typhoid and the like in humans, and calf scours and foot and mouth disease in animals can be treated with vaccines comprised of the polypeptides or polypeptide conjugates described herein. The vaccines are administered in a pharmaceutically acceptable adjuvant, carrier or diluent such as vegetable oil, as an alum precipitate in saline in synthetic oils, or even in mineral oil/with emulsion glycopeptides, and/or bacterial cell wall/fragments, and the like.

The polypeptides, polypeptide conjugates and antibodies to these polypeptides and polypeptide conjugates of this invention are also useful in the detection and diagnosis of disease, particularly in providing high purity materials useful for calibration solutions for assay techniques, such as ELISA or EMIT.

The enzymes for use in diagnostic reagents, standards or kits can vary widely, depending on the ease of conjugation, turnover rate, and the physiological fluid in which the unknown (analyte) is to be measured. Representative enzymes of choice include hydrolases, nucleases, amidases, esterases and the like which are found in U.S. Pat. No. 3,817,837, which is incorporated herein by reference.

The methods and apparatus for labeling an antibody as described herein for use in a diagnostic reagent, standard or kit is found in U.S. Pat. No. 4,366,241, which is incorporated herein by reference.

The following examples serve to illustrate the invention. They should not be construed as narrowing it, or limiting its scope.

EXAMPLE 1

Preparation of Human Growth Hormone Fragment H-Tyr-Gly-Ala-Ser-Asp-Ser-Asn-Val-Tyr-Asp-Leu-Cys-OH In the reaction vessel of a Beckman 990 Peptide Synthesizer is placed 1.06 g (1.0 mmol) of Boc-Cys(BzlOMe)-O-Resin prepared from chloromethylpolystyrene-1%-divinylbenzene resin (1 mmol Cl/g resin) by reaction with Boc-Cys(BzlOMe)-OCs salt [(B. F. Gisin, Helv. Chim. Acta, 56, 1476 (1973)]. Amino acids are added sequentially to this resin by means of a synthesis program, as follows:

| Step | Action | Time | |
|---|---|---|---|
| 1 | $CH_2Cl_2$ wash | 1 time | 1.5 min |
| 2 | 50% $CF_3CO_2H/CH_2Cl_2$ deprotection | 1 time | 1.5 min |
| 3 | 50% $CF_3CO_2H/CH_2Cl_2$ deprotection | 1 time | 30 min |
| 4 | $CH_2Cl_2$ wash | 3 times | 1.5 min |
| 5 | 10% triethylamine/$CH_2Cl_2$ | 2 times | 1.5 min |
| 6 | $CH_2Cl_2$ wash | 3 times | 1.5 min |
| 7 | $N^\alpha$—Boc-amino acid solution | 1 time | add |
| 8 | N,N'—dicyclohexylcarbodiimide solution | 1 time | add |
| 9 | $CH_2Cl_2$ rinse and hold reaction coupling | 1 time | 2 hr |
| 10 | $CH_2Cl_2$ rinse add | 1 time | 1.5 min |
| 11 | $CH_2Cl_2$ wash | 3 times | 1.5 min |
| 12 | ethanol wash | 3 times | 1.5 min |
| 13 | $CH_2Cl_2$ wash | 3 times | 1.5 min |

Steps 1–13 complete a coupling cycle for one amino acid and completeness of the reaction is checked by the ninhydrin method of E. Kaiser, et al., Anal. Biochem., 34, 595 (1970).

The resin is coupled sequentially with about a 2.5 molar excess of each protected amino acid and DCC. Thus, the resin is treated during successive coupling cycles with 0.623 g of Boc-Leu-OH.$H_2O$;
0.806 g of Boc-Asp(Bzl)-OH;
0.703 g of Boc-Tyr($Cl_2$Bzl)-OH;
0.543 g of Boc-Val-OH;
0.586 g of Boc-Asn-OH;
0.738 g of Boc-Ser(Bzl)-OH;
0.806 g of Boc-Asp(OBzl)-OH;
0.738 g of Boc-Ser(Bzl)OH;
0.473 g of Boc-Ala-OH;
0.438 g of Boc-Gly-OH; and
0.703 g of Boc-Tyr($Cl_2$Bzl)-OH.

The resin is removed from the reaction vessel, washed with $CH_2Cl_2$, and dried in vacuo to yield 3.35 g of the protected polypeptide resin.

The polypeptide product is simultaneously removed from the resin and completely deprotected by treatment with anhydrous liquid HF. A mixture of 3.34 g of protected polypeptide resin and 3.5 ml of anisole (scavenger) in a Kel-F reaction vessel is treated with 20 ml of redistilled (from $CoF_3$) anhydrous liquid HF at 0° C. for 1 hour. The HF is evaporated under vacuum and the residue of H-Tyr-Gly-Ala-Ser-Asp-Ser-Asn-Val-Tyr-Asp-Leu-Cys-OH, as its HF salt, is washed with ether. The residue is then extracted with glacial acetic acid. The acetic acid extract is lyophilized to yield crude material.

Purification is achieved by preparative high performance liquid chromatography on a 205 mg sample using a 2.5×100 cm column of 20–40 micron octadecylsilylated silica (Merck Lichroprep $C_{18}$). The eluent is 83% 0.03M $NH_4OAc$/17% acetonitrile. In 2 runs a total of about 400 mg of crude material is purified. After three lyophilizations from water, 85 mg of pure H-Tyr-Gly-Ala-Ser-Asp-Ser-Asn-Val-Tyr-Asp-Leu-Cys-OH is obtained as the acetate salt $[\alpha]_D^{25}$—20.1° (c 0.6, HOAc).

EXAMPLE 2

Preparation of H-Tyr-Asp-Thr-Ser-Asp-Ser-Asp-Asp-Tyr-His-Leu-Cys-OH

Repeating the procedure of Example 1, using the Boc-Cys(BzlOMe)-O-Resin and substituting the following protected and unprotected amino acids:
0.623 g of Boc-Leu-OH.$H_2O$;
1.023 g of Boc-His(Tos)OH;
0.703 g of Boc-Tyr($Cl_2$Bzl)OH;
0.806 g of Boc-Asp(OBzl)-OH;

0.806 g of Boc-Asp(OBzl)-OH;
0.738 g of Boc-Ser(Bzl)-OH;
0.806 g of Boc-Asp(OBzl)-OH;
0.738 g of Boc-Ser(Bzl)-OH;
0.773 g of Boc-Thr(Bzl)-OH;

0.806 g of Boc-Asp(OBzl)-OH; and
0.703 g of Boc-Tyr(Cl₂Bzl)-OH
in the solid phase synthesis sequence, the polypeptide H-Tyr-Asp-Thr-Ser-Asp-Ser-Asp-Asp-Tyr-His-Leu-Cys-OH, is obtained in good yield as the acetate salt $[\alpha]_D^{25} -33.4°$ (c 0.8, HOAc).

EXAMPLE 3

Preparation of Human Prolactin Fragment

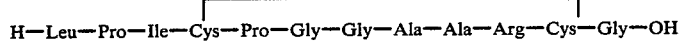

Repeating the procedure of Example 1 and substituting Boc-Gly-O-Resin for Boc-Cys(BzlOMe)-O-Resin and the following protected and unprotected amino acids:
1.708 g of Boc-Cys(Bzl-OMe)-OH;

2.142 g of Boc-Arg-OH:
0.946 g of Boc-Ala-OH;
0.946 g of Boc-Ala-OH;
0.876 g of Boc-Gly-OH;
0.876 g of Boc-Gly-OH;
1.706 g of Boc-Pro-OH;
1.708 g of Boc-Cys(BzlOMe);
1.146 g of Boc-Ile-OH.½H₂O;
1.706 g of Boc-Pro-OH; and
1.246 g of Boc-Leu-OH.H₂O;
in the solid phase synthesis sequence, the following polypeptide: H-Leu-Pro-Ile-Cys-Pro-Gly-Gly-Ala-Ala-Arg-Cys-Gly-OH is obtained in good yield as the acetate salt.

A solution of 0.67 g of the reduced forms of the polypeptide in a mixture of 330 ml H₂O and 280 ml acetone at pH 6.5 is treated with 172 mg of diiodoethane in 40 ml of acetone. The oxidative cyclization is complete after 2.5 hr. The mixture is concentrated to dryness, the residue is dissolved in H₂O, and the polypeptide is converted to the acetate salt by passage through an AG3 (-OAc form) weakly basic ion exchange resin (BioRad Labs, Inc.). The eluent is lyophilized to yield 0.64 g of the crude disulfide. Pure product is obtained by four prep-HPLC run on about 150-mg batches of crude material on a 2.5×100 cm column of Licroprep C-18 (25–40 micron) packing material using 16% CH₃CN/84% H₂O (0.03 M in NH₄OAc, pH 4.5) as eluent. Lyophilization yielded the cyclic product disulfide:

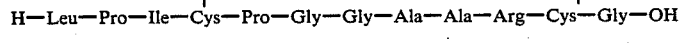

as 66 mg of white powder, $[\alpha]_D^{25} -96.8°$ (C 0.64, HOAc).

EXAMPLE 4

Preparation of Human Prolactin Fragment

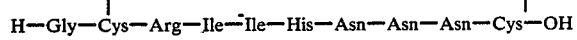

Repeating the procedure of Example 3 using Boc-Cys(BzlOMe)-O-resin and the following protected and unprotected amino acids:
1.16 g of Boc-Asn-OH;
1.16 g of Boc-Asn-OH;
1.16 g of Boc-Asn-OH;
2.052 g of Boc-His(Ts)-OH;
1.15 g of Boc-Ile-OH.½H₂O;
1.15 g of Boc-Ile-OH.½H₂O;
1.60 g of Boc-Arg(Ts)-OH;
1.708 g of Boc-Cys(Bzl-OMe)-OH; and
0.876 g of Boc-Gly-OH;
in the solid phase synthesis sequence, the following polypeptide:

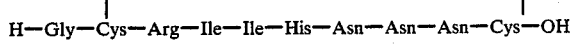

is obtained in good yield, $[\alpha]_D^{25} -67.1°$ (C 0.3, HOAc).

EXAMPLE 5

Preparation of a Human Growth Hormone Fragment
H-Ala-Ser-Asp-Ser-Asn-Val-Tyr-Asp-OH Repeating the procedure of Example 1 and substituting a Boc-Asp(OBzl)-O-Resin for Boc-Cys(BzlOMe)-O-Resin and the following protected and unprotected amino acids:
0.703 g of Boc-Tyr(Cl₂Bzl)-OH;
0.543 g of Boc-Val-OH;
0.586 g of Boc-Asn-OH;
0.738 g of Boc-Ser(Bzl)-OH;
0.806 g of Boc-Asp(OBzl)-OH;
0.738 g of Boc-Ser(Bzl)-OH; and
0.473 g of Boc-Ala-OH;
the following peptide is obtained: H-Ala-Ser-Asp-Ser-Asn-Val-Tyr-Asp-OH in good yield as the acetate salt.

EXAMPLE 6

Preparation of a Human Growth Hormone Fragment
H-Ala-Ser-Asp-Ser-Asn-Val-Tyr-Asp-Leu-Leu-Lys-Asp-Leu-Glu-OH Repeating the procedure of Example 1 and substituting a Boc-Glu-(OBzl)-O-Resin and the following protected and unprotected amino acids:
0.623 g of Boc-Leu-OH.H₂O;
0.806 g of Boc-Asp-(OBzl)OH;
0.951 g of Boc-Lys(Z)-OH;

0.623 g of Boc-Leu-OH.H$_2$O;
0.623 g of Boc-Leu-OH.H$_2$O;
0.806 g of Boc-Asp(Bzl)-OH;
0.703 g of Boc-Tyr (Cl$_2$Bzl)-OH;
0.543 g of Boc-Val-OH;
0.581 g of Boc-Asn-OH;
0.738 g of Boc-Ser(Bzl)-OH;
0.806 g of Boc-Asp-(OBzl)-OH;
0.738 g of Boc-Ser(Bzl)-OH; and
0.473 g of Boc-Ala-OH;
the following polypeptide is obtained: H-Ala-Ser-Asp-Ser-Asn-Val-Tyr-Asp-Leu-Leu-Lys-Asp-Leu-Glu-OH in good yield is the acetate salt.

EXAMPLE 7

Preparation of a Human Growth Hormone Fragment H-Asn-Ser-Leu-Val-Tyr-Gly-Ala-Ser-Asp-Ser-Asn-Val-Tyr-Asp-Leu-Leu-Lys-Asp-Leu-Glu-OH Repeating the procedure of Example 1 and substituting a Boc-Glu-O-Resin for Boc-Cys(BzlOMe)-O-Resin and the following protected and unprotected amino acids:
0.623 g of Boc-Leu-OH.H$_2$O;
0.806 g of Boc-Asp-(OBzl)-OH;
0.951 g of Boc-Lys-(Z)-OH;
0.623 g of Boc-Leu-OH H$_2$O;
0.623 g of Boc-Leu-OH H$_2$O;
0.806 g of Boc-Asp(Bzl)-OH;
0.703 g of Boc-Tyr(Cl$_2$Bzl)-OH;
0.543 g of Boc-Val-OH;
0.581 g of Boc-Asn-OH;
0.738 g of Boc-Ser(Bzl)-OH;
0.806 g of Boc-Asp-(OBzl)-OH;
0.738 g of Boc-Ser-(Bzl)-OH:
0.473 g of Boc-Ala-OH;
0.438 g of Boc-Gly-OH;
0.703 g of Boc-Tyr(CH$_2$Bzl)-OH;
0.543 g of Boc-Val-OH;
0.623 g of Boc-Leu-OH.H$_2$O;
0.738 g of Boc-Ser(Bzl)-OH; and
0.586 g of Boc-Asn-OH;
the following polypeptide is obtained: H-Asn-Ser-Leu-Val-Tyr-Gly-Ala-Ser-Asp-Ser-Asn-Val-Tyr-Asp-Leu-Leu-Lys-Asp-Leu-Glu-OH in good yield as the acetate salt.

EXAMPLE 8

Preparation of a Human Growth Hormone Fragment H-Asn-Ser-Leu-Val-Tyr-Gly-Ala-Ser-Asp-Ser-Asn-Val-Tyr-Asp-OH Repeating the procedure of Example 1 and substituting a Boc-Asp-(OBzl)-O-Resin for Boc-Cys(BzlOMe)-O-Resin and the following protected and unprotected amino acids:
0.703 g of Boc-Tyr(Cl$_2$Bzl)-OH;
0.543 g of Boc-Val-OH;
1.16 g of Boc-Asn-OH;
0.738 g of Boc-Ser(Bzl)-OH;
0.806 g of Boc-Asp-(OBzl)-OH;
0.738 g of Boc-Ser(Bzl)-OH;
0.473 g of Boc-Ala-OH;
0.438 g of Boc-Gly-OH;
0.703 g of Boc-Tyr(CH$_2$Bzl)-OH;
0.543 g of Boc-Val-OH;
0.623 g of Boc-Leu-OH.H$_2$O;
0.738 g of Boc-Ser(Bzl)-OH; and
0.586 g of Boc-Asn-OH;
the following polypeptide is obtained: H-Asn-Ser-Leu-Val-Tyr-Gly-Ala-Ser-Asp-Ser-Asn-Val-Tyr-Asp-OH in good yield as the acetate salt.

EXAMPLE 9

Maleimide Conjugated Bovine Gamma Globulin and Bovine Serum Albumin (M-BGG/M-BSA)

A. A 20-mg portion of bovine gamma globulin (BGG) in 5 ml of pH 6.73 phosphate buffer is treated with 4 mg of succinimidyl 4-(p-maleimidophenyl)butyrate (SMPB, Pierce Chem Co.) in 100 μl of DMF. The mixture is stirred at 25° C. for 1.5 hr and centrifuged. The supernatant liquid is desalted on a Sephadex G-25 column by elution with H$_2$O the first UV absorbing peak (Abs 2.01 OD at 280 nm) is pooled to yield 20 ml of standard solution of M-BGG [4-(p-maleimidophenyl)butryamido-BGG].

Similarly, by replacing the BGG with BSA is obtained the corresponding M-BSA.

EXAMPLE 10

Human Somatotropin (Growth Hormone) Fragment Conjugates (HGH-M-BGG/HBH-M-BSA)

A 2 mg sample of H-Tyr-Gly-Ala-Ser-Asp-Ser-Asn-Val-Tyr-Asp-Leu-Cys-OH is dissolved in 10 ml of standard solution of M-BGG and stirred at 25° C. overnight. The reaction product (wherein the —SH of the cysteine has added to the carbon-carbon double bond) is purified by gel permeation chromatograph on a Sephadex G-25 column by elution with H$_2$O. The first UV absorbing peak is pooled and lyophilized to give the protein conjugated human somatotropin conjugate (immunogen) as a white powder. Amino acid analysis of the product indicated about 20 molecules of the polypeptide fragment per molecule of BGG in the conjugate.

Similarly, by replacing the M-BGG by M-BSA is obtained the HGH-M-BSA conjugate.

EXAMPLE 11

Human Growth Fragment Conjugate

By replacing the polypeptide of Example 5 containing the eight amino acid sequence with a stoichiometrically equivalent amount of the polypeptide of Example 10 and completing the procedure of Example 10, there is obtained the corresponding polypeptide-M-BGG or polypeptide-M-BSA conjugate.

EXAMPLE 12

Human Growth Hormone Fragment Conjugate

By replacing the polypeptide of Example 6 containing the fourteen amino acid sequence with a stoichiometrically equivalent amount of the peptide of Example 10 and using the procedure of Example 10, there is obtained the corresponding polypeptide-M-BGG conjugate or polypeptide-M-BSA conjugate.

EXAMPLE 13

Human Growth Hormone Fragment Conjugate

By replacing the polypeptide of Example 7 containing the twenty amino acid sequence with a stoichiometrically equivalent of the peptide of Example 10 and using the procedure of Example 10, there is obtained the corresponding polypeptide-M-BGG conjugate or polypeptide-M-BSA conjugate.

EXAMPLE 14

Human Growth Hormone Fragment Conjugate

By replacing the polypeptide of Example 8 containing the fourteen amino acid sequence with a stoichiometrically equivalent amount of the peptide of Example 10 and using the procedure of Example 10, there is obtained the corresponding polypeptide-M-BGG conjugate or polypeptide-M-BSA conjugate.

EXAMPLE 15

Human Placental Lactogen (Somatomamotropin) - Conjugates (HPL-M-BGG/HPL-M-BSA)

A 2 mg sample of H-Tyr-Asp-Thr-Ser-Asp-Ser-Asp-Asp-Tyr-His-Leu-Cys-OH is dissolved in 10 ml of the standard solution of M-BGG and stirred at 25° C. overnight. The reaction product is purified by gel permeation chromatography on a Sephadex G-25 column by elution with H$_2$O. The earliest eluting UV absorbing (280 mm) peak is pooled and lyophilized to yield the protein carrier coupled to the human placental lactogen fragment. Amino acid analysis of the product indicated that about 20 molecules of the polypeptide fragment is coupled to each molecule of M-BGG.

Similarly, by replacing the M-BGG with M-BSA, there is obtained the HPL-M-BSA conjugate.

EXAMPLE 16

Human Prolactin Fragment Conjugates (HP-N-BGG/HP-N-BSA/HP-C-BGG/HP-C-BSA)

A 7 mg portion of

H—Leu—Pro—Ile—Cys—Pro—Gly—Gly—Ala—Ala—Arg—Cys—Gly—OH (Human Prolactin C-terminus disulfide loop; HP—N) or

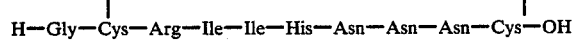

H—Gly—Cys—Arg—Ile—Ile—His—Asn—Asn—Asn—Cys—OH (Human Prolactin C-terminus disulfide loop; HP—C)

is treated with 15 mg of BGG and 10 mg of N-ethyl-N'-dimethylaminopropylcarbodiimide in 5 ml of NaOAc buffer (pH 4.65).

The material is desalted by gel permeation chromatography on a Sephadex G-25 column in H$_2$O. The first ultraviolet absorbing peak is pooled and lyophilized to yield HP-N-BGG or HP-C-BGG as a white powder.

Similarly, by replacing the BGG by BSA one obtains the corresponding HP-N-BSA or HP-C-BSA conjugates.

EXAMPLE 17

Injection of Host with Peptide Immunogen

A portion of the polypeptide conjugate is dissolved in 0.9% saline and emulsified with complete Freunds' Adjuvant (mineral oil containing whole mycobacteria plus emulsifier) by the "two syringe technique" recommended by the supplier (Gibco). The mixture is injected subcutaneously into the host animal at multiple sites. The animal is boosted with immunogen in Incomplete Freund's Adjuvant (IFA) at several week intervals until the desired immunological response is achieved.

For example, a 2 mg sample of the human Ifγ-BGG conjugate is dissolved in 1 ml of saline and emulsified with 3 ml of Freunds Complete Adjuvant. The resultant vaccine is divided into 4 portions and a 2.2 kg female rabbit is injected subcutaneously in each shoulder and hip region. The animal is boosted at week 3 with 0.1 mg of conjugate in ½ ml of IFA by subcutaneous injection as above. After a further 3 weeks the animal is bled to obtain serum for the ELISA assay and 1 week later is boosted again. The pattern of boost, wait 3 weeks, bleed, wait 1 week, boost is continued through 5 cycles.

The blood sera collected is allowed to clot at 25° C. for several hours. The clear serum is separated from the clot by centrifugation and is diluted with 0.9% saline to the desired concentration.

While the present invention has been described with reference to the specific embodiments thereof, it should be understood by those skilled in this art that various changes may be made and equivalents may be substituted without departing from the true spirit and scope of the invention. In addition, many modifications may be made to adopt a particular situation, material, or composition of matter, process, process step or steps, or the present objective to the spirit and scope of the invention. In addition, many modifications may be made to adopt a particular situation, material, or composition of matter, process, process step or steps, or the present objective to the spirit of this invention without departing from its essential teachings.

What is claimed is:

1. A method of producing a synthetic antigenic polypeptide from a protein having a predetermined sequence of amino acids, said method comprising the steps of:
   (1) determining a predicted β-turn polypeptide sequence consisting of four amino acid residues of the protein, said β-turn sequence having two ends; and
   (2) synthesizing a polypeptide segment of the protein, wherein said segment comprises the β-turn sequence and from two to eight amino acid residues on each end of the β-turn sequence.

2. The method of claim 1 which further includes the step of conjugating said polypeptide with a macromolecular carrier.

3. A synthetic antigenic polypeptide which is a determinant site of a protein, said polypeptide consisting of from 8 to 20 amino acid residues, having an amino-terminal amino acid and a carboxyl-terminal amino acid, wherein said polypeptide includes:
   (a) a four amino acid sequence which corresponds to the four amino acid sequence of a predicted β-turn of said protein;
   (b) a sequence of two to eight amino acid residues attached to the amino terminal of said four amino acid sequence; and
   (c) a sequence of two to eight amino acid residues attached to the carboxyl terminal of said four amino acid sequence;

wherein the amino acid residues of subparts (b) and (c) correspond to those attached to the amino terminal and the carboxyl terminal, respectively of the β-turn of said protein, or a pharmaceutically acceptable salt of said polypeptide.

4. The method of claim 1 wherein the four amino acid sequence of the β-turn has a calculated probability greater than or equal to $0.75 \times 10^{-4}$.

5. The polypeptide of claim 3 wherein the four amino acid sequence of the β-turn has a calculated probability greater than or equal to $0.75 \times 10^{-4}$.

* * * * *